United States Patent [19]
Welch

[11] Patent Number: 5,807,281
[45] Date of Patent: Sep. 15, 1998

[54] CERVICAL RING TO DETECT LABOR

[76] Inventor: Robert A. Welch, 9573 Winterset Cir., Plymouth, Mich. 48170

[21] Appl. No.: 723,101

[22] Filed: Oct. 1, 1996

[51] Int. Cl.⁶ .............................................. A61B 5/03
[52] U.S. Cl. ................................. 600/588; 600/591
[58] Field of Search ............................ 600/587, 588, 600/591

[56] References Cited

U.S. PATENT DOCUMENTS

| | | |
|---|---|---|
| 4,476,871 | 10/1984 | Hon . |
| 4,719,925 | 1/1988 | Parsons . |
| 4,936,316 | 6/1990 | Jewett . |
| 4,967,761 | 11/1990 | Nathanielsz . |
| 5,301,680 | 4/1994 | Rosenberg . |
| 5,338,297 | 8/1994 | Kocur et al. . |
| 5,373,852 | 12/1994 | Harrison et al. . |
| 5,406,961 | 4/1995 | Artal . |
| 5,450,857 | 9/1995 | Garfield et al. . |
| 5,483,970 | 1/1996 | Rosenberg . |

*Primary Examiner*—Max Hindenburg
*Assistant Examiner*—Pamela L. Wingood
*Attorney, Agent, or Firm*—Howard & Howard

[57] ABSTRACT

The present invention relates to a method and an assembly (10) for detecting dilation of a cervix (74) of a pregnant female (78) at the onset of labor. The assembly (10) includes a ring-shaped element (16) in series with an enclosure (12) which encircles the cervix (74). The enclosure (12) contains a readily detectable fluid or particulate material (14). When the cervix (74) dilates at the onset of labor, the force of dilation is transmitted by the ring-shaped element (16) of the assembly (10) to the enclosure (12) and opens the enclosure (12) causing release of the material (14). The assembly (10) also includes a series of friction tabs (18) to keep the assembly (10) in place on the cervix (74).

The method involves selecting an appropriately sized assembly (10), placing the assembly (10) on the cervix (74) of the pregnant female (78), and detecting the release of the material (14) which signals that labor has begun.

34 Claims, 2 Drawing Sheets

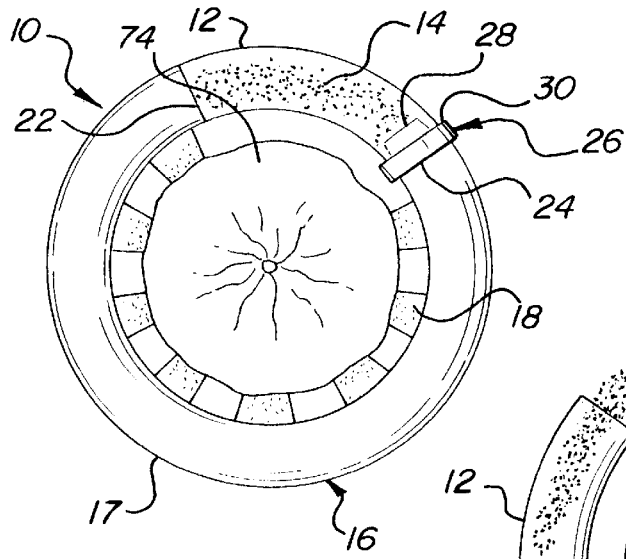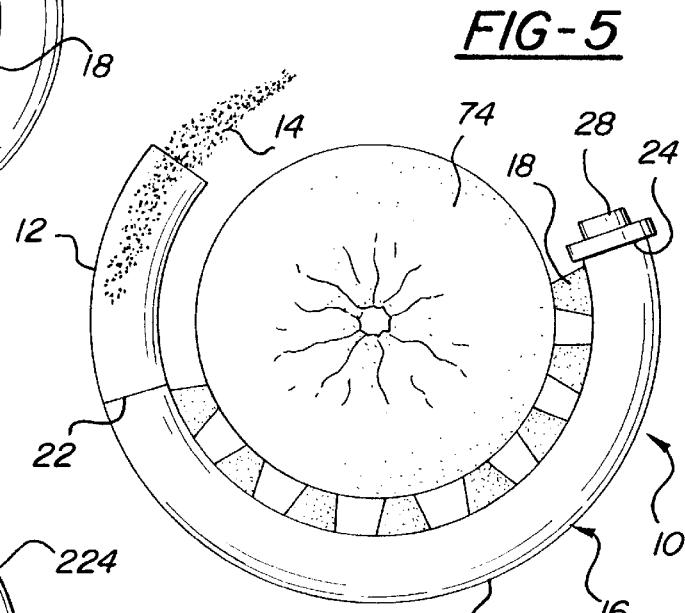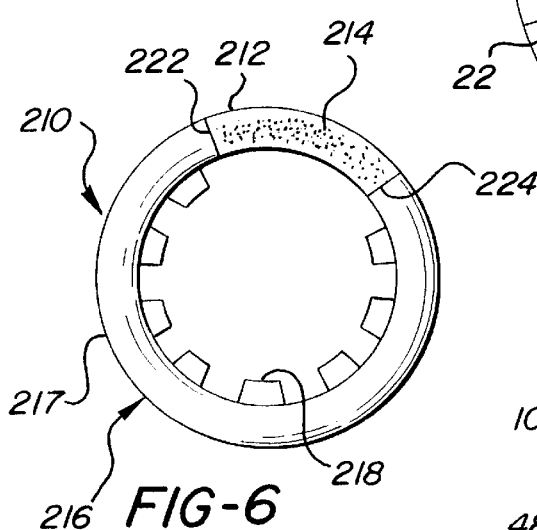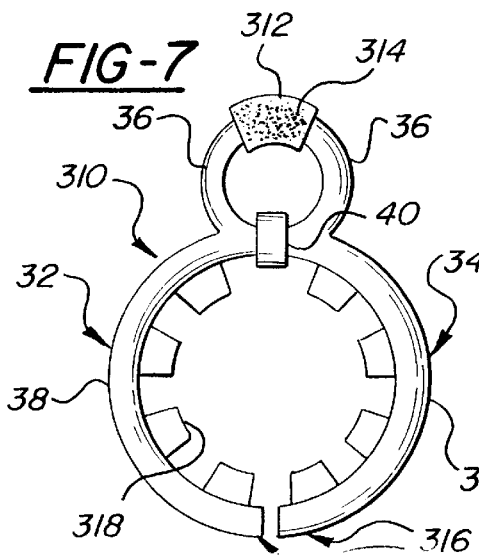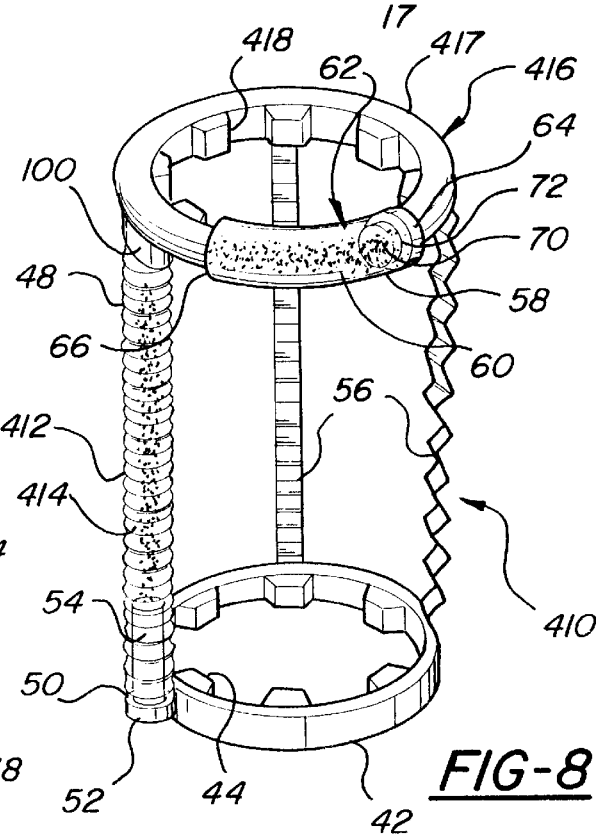

CERVICAL RING TO DETECT LABOR

TECHNICAL FIELD

The present invention relates generally to a method and a device for detecting the onset of labor in a pregnant female by monitoring cervical dilation. More specifically, the invention is a device which measures the force exerted by the cervix as it dilates at the onset of labor and then releases a material to signal that cervical dilation has occurred, the method involves inserting the device into the vagina and over the cervix of a pregnant female and monitoring release of the material to detect the onset of labor.

BACKGROUND OF THE INVENTION

Often during pregnancy, repeated trips to the hospital labor and delivery room or emergency room occur because the female believes labor has begun. Many times these are "false alarms" and the female is sent home to wait. The only way to accurately determine when labor has begun is through a detection that the cervix has begun to dilate. Typically this detection is accomplished by a digital pelvic examination of the cervix by the physician. These "false alarms" can lead to frustration and embarrassment for the pregnant female. Other times a pregnant female may not have enough warning to allow her to get to the hospital in time and the baby is delivered in a car or elsewhere. Finally, statistics show that about 17% of babies deliver prematurely, some of which might be prevented if the physician were able to intervene in time. Currently, there exist a number of devices for monitoring cervical dilation. Unfortunately, most require that the female remain in the hospital while the device is being used to monitor the cervix, or require that the pregnant female wear a radio receiver to detect the dilation of the cervix. All of the devices are expensive and quite inconvenient.

SUMMARY OF THE INVENTION AND ADVANTAGES

The invention includes a method for detecting dilation of a cervix (74) in a vagina (76) of a pregnant female (78) during labor wherein the method comprises the steps of encapsulating a first material (14) in a first enclosure (12) for release in response to a predetermined force and the method is characterized by transmitting the predetermined force from the cervix (74) in response to dilation of the cervix (74) to release the first material (14).

The invention further comprises an assembly (10) for detecting dilation of a cervix (74) in a vagina (76) of a pregnant female (78) during labor, wherein the assembly (10) comprises; a first enclosure (12) containing a first material (14) for releasing the first material (14) in response to a predetermined force; and the assembly (10) is characterized by a first element (16) for transmitting the predetermined force from the cervix (74) in response to the dilation of the cervix (74) to release the first material (14). The present invention, by contrast to the current means for measuring cervical dilation, is very simple to use and inexpensive to manufacture. The assembly (10) can be placed on the cervix during one of the normal pre-natal visits to the physician and the pregnant female can continue her normal routine. Once in place the assembly (10) requires no maintenance and is unlikely to suffer from malfunctions. The assembly (10) provides an easily monitored and detected signal when the cervix has dilated thereby reducing the possibility of "false alarms", no warning, or premature delivery.

BRIEF DESCRIPTION OF THE DRAWINGS

Other advantages of the present invention will be readily appreciated as the same becomes better understood by reference to the following detailed description when considered in connection with the accompanying drawings wherein:

FIG. 4 is a head on view of a tube design embodiment of the invention encircling a non-dilated cervix;

FIG. 5 is a head on view of a tube design embodiment of the invention after dilation of the cervix has caused release of the material;

FIG. 6 is a top view of a rupture design embodiment of the invention;

FIG. 7 is a top view of a compression design embodiment of the invention; and

FIG. 8 is a side view of a combination tube design and cervical shortening embodiment of the invention.

DETAILED DESCRIPTION OF THE PREFERRED EMBODIMENT

Figure 2:
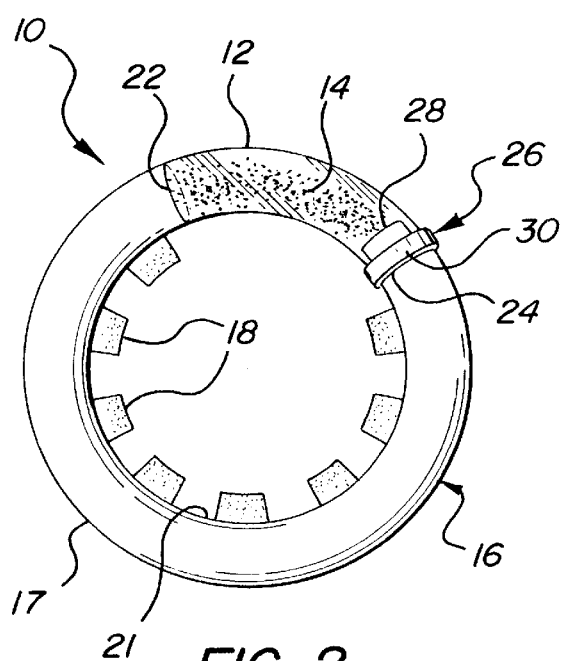
FIG. 2 is a top view of a tube design embodiment of the invention.

Referring to the FIGS. 2, 3, and 6–8, wherein like numerals indicate like or corresponding parts throughout the several views, an assembly 10 for detecting dilation of a cervix 74 in a vagina 76 of a pregnant female 78 during labor is shown generally in FIG. 2. The assembly 10 comprises; a first enclosure 12 containing a first material 14 for releasing the first material 14 in response to a predetermined force.

The assembly 10 is characterized by a first element 16 for transmitting the predetermined force from the cervix 74 in response to the dilation of the cervix 74 to release the first material 14. The assembly 10 is designed so that the first element 16 can encircle the cervix 74. The force is caused by the dilation of the cervix 74 which accompanies the onset of labor. During labor the diameter of the cervix 74 increases dramatically in order to accommodate the exit of an offspring 80 from the uterus 82 of the pregnant female 78. The first element 16 must be have the property of limited elasticity in order to transmit the force of cervical dilation and cause release of the first material 14. It will be appreciated by anyone of ordinary skill in the art that a variety of plastics have the property of limited elasticity and that the first element 16 and the first enclosure 12 could be formed from a single piece of plastic. Additionally, anyone of ordinary skill in the art will appreciate that a plurality of diameters of the assembly 10 will be required in order to accommodate the range of sizes of undilated cervixes that may be found in any population of females. It is medically important to select a diameter which will be large enough to encircle the cervix 74, remain in place during normal movements of the female and not impede blood flow throughout the cervix 74 while the assembly 10 is on the cervix 74.

The assembly 10 further includes on the first element 16 a retaining means 18 for retaining the first element 16 on the cervix 74. In the assembly 10 shown, the retaining means 18 comprises a first set of friction tabs. It will be appreciated by one of ordinary skill in the art that the retaining means 18 could be achieved in many other ways such as placing friction tabs outside the first element 16 and projecting toward the inside of the first element 16, the friction could also be provided by manufacturing the first element 16 from a substance or coating it with a substance which provides friction between the first element 16 and the cervix 74. Alternatively, the interior circumference 21 of the first element 16 could be scored or have a rough surface to provide the necessary friction.

In the assembly 10 shown the first enclosure 12 and the first element 16 are in series. The first element 16 is shown as a first ring 17 with a first end 22 and a second end 24 with the first enclosure 12 being disposed between the first end 22 and the second end 24 to open the first enclosure 12.

In the assembly 10, the second end 24 of the first ring 17 is a plunger 26 which closes the first enclosure 12. The plunger 26 shown includes a projection 28 which inserts into the first enclosure 12 and a shoulder 30 which acts as a stop to prevent further insertion of the second end 24 into the first enclosure 12. It will be appreciated by one of ordinary skill in the art that alternatively the second end 24 could be tapered to fit directly into the first enclosure 12. The first enclosure 12 is impervious to prevent leakage of the first material 14. The first material 14 can be a fluid or a particulate material. The fluid could be a liquid of a predetermined color chosen so that release of the liquid would be readily detectible. Examples of such a liquid include ordinary dyes such as Evans blue, Indigo Carmine, or food coloring dyes. Or the fluid could be an odoriferous gas which could also be readily detected upon release from the first enclosure 12. The particulate material chosen could be a granular form of a dye which could react with bodily fluids to produce a readily detectable liquid or stain.

Figure 3:
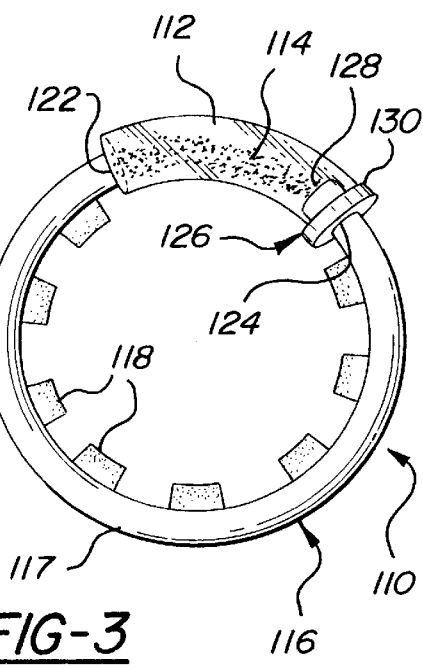
FIG. 3 is a top view of a band design embodiment of the invention.

An alternative embodiment of the assembly 110 is shown in FIG. 3, wherein the only difference from the embodiment shown in FIG. 2 is that the first element 116 is in the shape of a band with the first enclosure 112 of a larger diameter than the band.

An alternative embodiment of the assembly 210 is shown in FIG. 6 wherein the only difference from the embodiment shown in FIG. 2 is that the first element 216 is a first ring 217 with a first end 222 and a second end 224 wherein the first end 222 and the second end 224 of the first ring 217 are attached to the first enclosure 212 for rupturing the first enclosure 212. The first enclosure 212 in this embodiment is designed to rupture in response to the force caused by dilation of the cervix 74.

An alternative embodiment of the assembly 310 is shown in FIG. 7 wherein there are the following differences from the embodiment shown in FIG. 2. The first enclosure 312 and the first element 316 are in parallel, the first element 316 comprises a pair of arms 32 and 34 each arm comprised of an upper 36 and a lower 38 arc. The arms 32 and 34 are joined at the intersection of their upper 36 and lower 38 arcs by a mechanism 40 which permits the arms 32 and 34 to pivot such that as the lower arcs 38 move away from each other in response to the force of the cervix 74 dilating the upper arcs 36 move toward each other and compress the first enclosure 312 and the first enclosure 312 eventually ruptures in response to a predetermined force. The mechanism 40 can be a simple joining of the two arms, 32 and 34, with a material of greater elasticity than the arms, 32 and 34, or the mechanism 40 could be a shaped joint such that the arms, 32 and 34, remain joined yet can pivot.

An alternative embodiment of the assembly 410 is shown in FIG. 8. During labor the cervix 74 not only dilates, but it also [elongates] shortens. This embodiment allows one to monitor both dilation and shortening of the cervix 74. The assembly 410 comprises, in addition to a first element 416, a second element 42 for transmitting a predetermined force from the cervix 74. The second element 42 also encircles the cervix 74. The second element 42 includes an additional retaining means 44 for retaining the second element 42 on the cervix 74, in the embodiment shown the retaining means 44 comprise a second set of friction tabs. The first element 416 and the second element 42 are parallel to each other and the first enclosure 412 is placed between the first element 416 and the second element 42 along the longitudinal axis of the cervix 74 to open the first enclosure 412 in response to compression forces. The first enclosure 412 includes a first material 414 as explained and illustrated above. In the assembly 410 as shown, the first enclosure 412 is accordion-shaped and its length can be significantly shortened by compression along its longitudinal axis. The first enclosure 412 has a first end 48 and a second end 50 and the first end 48 of the first enclosure 412 is attached along a portion of the of the first enclosure 412 to the first element 416. The first end 48 is closed by a displaceable barrier means 100. The displaceable barrier means 100 could be either a thin membrane for rupturing or a plug. The second end 50 of the first enclosure 412 is attached to the second element 42 for closing the first enclosure 412. In the assembly 410 as shown the second element 42 includes a plunger 52 for closing the second end 50 of the first enclosure 412. The plunger 52 has a projection 54 which is inserted into the second end 50 of the first enclosure 412. It will be appreciated by one of ordinary skill in the art that the plunger 52 could be created in a number of different forms as explained and illustrated above. The first element 416 and the second element 42 are joined by the first enclosure 412 and a set of connectors 56. The connectors 56 serve to maintain the parallel spatial relationship between the first element 416 and the second element 42. As the cervix 74 shortens at the onset of labor, the first element 416 and the second element 42 will be forced toward each other causing a compression of the first enclosure 412 along its longitudinal axis. In the embodiment shown, the compression would drive the projection 54 and the first material 414 toward the first end 48 and displace the displaceable barrier means 100 to release the first material 414. Alternatively, the first enclosure 412 could be in the form of a telescoping tube rather than an accordion-shaped tube. In addition, the positions of the first end 48 and the second end 50 with its plunger 52 and projection 54 could be reversed.

The assembly 410 can be constructed as described thus far in which the assembly 410 only functions to respond to cervical shortening. Additionally, the assembly 410 can be constructed as illustrated in FIG. 8, wherein a second enclosure 58 containing a second material 60 and the first element 416 are in series and the first element 416 is a first ring 417 with a first end 66 and a second end 64 with the second enclosure 58 being disposed between the first 66 and the second ends 64 to open the second enclosure 58. In the assembly 410 shown the second end 64 of the first ring 417 is a plunger 62 having a projection 70 and a shoulder 72. As will be appreciated by one of ordinary skill in the art the assembly 410 could also be constructed wherein the first element 416 is a first ring 417 with a first end 66 and a second end 64; and wherein the first end 66 and the second end 64 of the first ring 417 are attached to the second enclosure 58 for rupturing the second enclosure 58 to release the second material 60. The second material 60 could take any of the forms described above for the first material 14.

Figure 1:
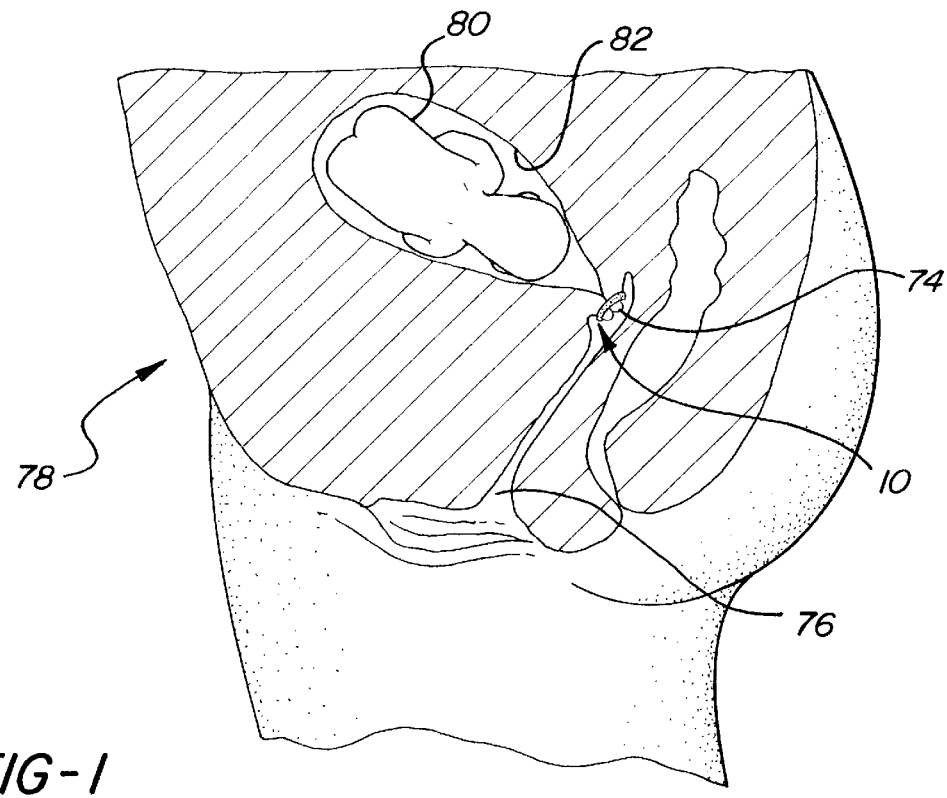
FIG. 1 is a cross-sectional side view of a pregnant human female with an embodiment of the assembly in place.

FIGS. 1, 4, and 5 illustrate the method for detecting dilation of a cervix 74 in a vagina 76 of a pregnant female 78, generally shown in cross-section, during labor. The method comprises the steps of; encapsulating a first material 14 in a first enclosure 12 for release in response to a predetermined force. The force is caused by the dilation of the cervix 74 which accompanies the onset of labor. During labor the diameter of the cervix 74 increases dramatically in order to accommodate the exit of an offspring 80 from the uterus 82 of the pregnant female 78. The method is characterized by transmitting the predetermined force from the cervix 74 in response to dilation of the cervix 74 to release the first material 14. The method is further characterized by at least partially encircling the cervix 74 with an assembly 10 which includes a first force transmitting element 16 in the shape of a ring 17 for transmitting the predetermined force from the cervix 74 to the first enclosure 12 to release the first material 14 from the first enclosure 12. The sequence of events is illustrated in FIGS. 4 and 5. A health care provider places an appropriately sized assembly 10 on the cervix 74, typically near the end of the gestation period of the pregnancy. At the onset of labor, the cervix 74 begins to dilate to accommodate exit of the offspring 80. The force caused by the dilation of the cervix 74 expands the first element 16 and leads to release of the first material 14. The release of the first material 14 is detected signaling that the cervix 74 has begun to dilate. In practicing the method as set forth the encapsulated first material 14 can be a fluid, a liquid of a predetermined color, or a particulate material. In practicing the method, the encircling of the cervix 74 comprises placing the first force transmitting ring 16 snugly around the cervix 74. The first force transmitting ring 16 and the first enclosure 12 may be placed in series, so that the first enclosure 12 will open in response to opening tension forces caused by dilation of the cervix 74. Alternatively, the first ring 17 and the first enclosure 12 could be placed in parallel, so that the first enclosure 12 opens in response to compression forces caused by dilation of the cervix 74.

In addition, the method can be further characterized by placing a second force transmitting ring 42 snugly around the cervix 74 parallel to the first force transmitting ring 68 and placing the first enclosure 12 between the two rings along the longitudinal axis of the cervix 74 to open the first enclosure 12 in response to compression forces caused by shortening of the cervix 74. The method as set forth could also include placing a second enclosure 58, containing a second material 60, in series with the first force transmitting ring 68, to open the second enclosure 58 in response to opening tension forces caused by dilation of the cervix 74.

In practicing the method it will be understood by one of ordinary skill in the art that snugly fitting the first element 16 and a second element 42 about the cervix 74 requires selecting elements which are sized such that they will remain in place on the cervix 74 during all normal bodily movements of the pregnant female 78 and be able to respond to dilation of the cervix 74 by releasing the first material 14 and the second material 60, yet not be so tight that the elements impede blood flow throughout the cervix 74. The method will require a multiple number of elements of different diameters to accommodate the range of non-dilated cervix 74 sizes which would be found in any population of females. The use of the method and assembly 10 are not restricted to pregnant human females. The assembly 10 and method can easily be adapted to use in many other species when it is desired to know the onset of cervical dilation. This could be especially useful in the field of veterinary medicine. Often it is important for the veterinarian or the animal owner to know when dilation of the cervix 74 has occurred. The assembly 10 could be put in place by the veterinarian or the animal owner.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, wherein reference numerals are merely for convenience and are not to be in any way limiting, the invention may be practiced otherwise than as specifically described.

What is claimed is:

1. A method for detecting dilation of a cervix (74) in a vagina (76) of a pregnant female (78) during labor said method comprising the steps of:

encapsulating a first material (14) in a first enclosure (12) for release in response to a predetermined force, said method characterized by transmitting the predetermined force directly from the cervix (74) in response to dilation of the cervix (74) to release the first material (14) for flow out of the vagina (76) and detection by the pregnant female (78).

2. A method as set forth in claim 1 further characterized by at least partially encircling the cervix (74) with a first force transmitting element (16) for transmitting the predetermined force from the cervix (74) to the first enclosure (12) to release the first material (14) from the first enclosure (12)

3. A method as set forth in claim 2 wherein the encapsulating of the first material (14) is further characterized by encapsulating a fluid.

4. A method as set forth in claim 2 wherein the encapsulating of the first material (14) is further characterized by encapsulating a liquid of a predetermined color.

5. A method as set forth in claim 2 wherein the encapsulating of the first material (14) is further characterized by encapsulating a particulate material.

6. A method as set forth in claim 2 wherein the encircling of the cervix (74) comprises placing a first force transmitting ring (17) snugly around the cervix (74).

7. A method as set forth in claim 6 further defined as placing the first force transmitting ring (17) and the first enclosure (12) in series, to open the first enclosure (12) in response to opening tension forces.

8. A method as set forth in claim 6 further defined as placing the first ring (17) and the first enclosure (12) in parallel, to open the first enclosure (12) in response to compression forces.

9. A method as set forth in claim 6 further characterized by placing a second force transmitting ring (42) snugly around the cervix (74) adjacent to the first force transmitting ring (417) and placing the first enclosure (412) between the two rings along the longitudinal axis of the cervix (74) to open the first enclosure (412) in response to compression forces.

10. A method as set forth in claim 9 further defined as placing a second enclosure (58) in series with the first force transmitting ring (417), to open the second enclosure (58) in response to opening tension forces.

11. A method as set forth in claim 10 wherein the second enclosure (58) contains a second material (60).

12. An assembly (10) for detecting dilation of a cervix (74) in a vagina (76) of a pregnant female (78) during labor, wherein said assembly (10) comprises;

a first enclosure (12) containing a first material (14) for releasing said first material (14) into the vagina (76) in response to a predetermined force; and said assembly (10) characterized by a first element (16) for encircling the cervix (74) and transmitting said predetermined force directly from the cervix (74) in response to the dilation of the cervix (74) to release said first material (14).

13. An assembly (10) as set forth in claim 12 wherein said first element (16) has a retaining means (18) for retaining said first element (16) on the cervix (74).

14. An assembly (10) as set forth in claim 13 wherein said retaining means (18) comprises a first set of friction tabs.

15. An assembly (10) as set forth in claim 12 wherein said first enclosure (12) and said first element (16) are concentric arcs.

16. An assembly (10) as set forth in claim 15 wherein said first element (16) is a first ring (17) with a first end (22) and a second end (24); said first enclosure (12) being disposed between said first (22) and said second ends (24), said second end (24) to open said first enclosure (12).

17. An assembly (10) as set forth in claim 16 wherein said second end (24) of said first ring (17) is a plunger (26) closing said first enclosure (12).

18. An assembly (210) as set forth in claim 15 wherein said first element (216) is a first ring (217) with a first end (222) and a second end (224); and wherein said first end (222) and said second end (224) of said first ring (217) are attached to said first enclosure (212) for rupturing said first enclosure (212).

19. An assembly (310) as set forth in claim 12 wherein said first enclosure (312) and said first element (316) are adjacent.

20. An assembly (310) as set forth in claim 19 wherein said first element (316) includes a pair of upper arcs (36) that contact said first enclosure (312) and a mechanism (40) for compressing said first enclosure (312) in response to a predetermined force.

21. An assembly (310) as set forth in claim 20 wherein said mechanism (40) is a pivot.

22. An assembly (10) as set forth in claim 12 wherein said first enclosure (12) is impervious and said first enclosure (12) includes a fluid.

23. An assembly (10) as set forth in claim 22 wherein said fluid comprises a liquid of a predetermined color.

24. An assembly (10) as set forth in claim 12 wherein said first material (14) is a particulate material.

25. An assembly (410) as set forth in claim 12 further characterized as including a second element (42) for transmitting said predetermined force; said second element (42) encircling the cervix (74).

26. An assembly (410) as set forth in claim 25 wherein said second element (42) includes an additional retaining means (44) for retaining said second element (42) on the cervix (74).

27. An assembly (410) as set forth in claim 26 wherein said additional retaining means (44) comprises a second set of tabs.

28. An assembly (410) as set forth in claim 25 wherein said first element (416) and said second element (42) are adjacent to each other and said first enclosure (412) is placed between said first element (416) and said second element (42) along the longitudinal axis of the cervix (74) to open said first enclosure (412) in response to compression forces.

29. An assembly (410) as set forth in claim 28 wherein said first enclosure (412) has a first end (48) and a second end (50) and further wherein said first end (48) of said first enclosure (412) is attached to said first element (416) and said second end (50) of said first enclosure (412) is attached to said second element (42) for opening said first enclosure (412).

30. An assembly (410) as set forth in claim 29 wherein said second element (42) includes a plunger (52) for closing said second end (50) of said first enclosure (412).

31. An assembly (410) as set forth in claim 28 wherein a second enclosure (58) and said first element (416) are concentric arcs.

32. An assembly (410) as set forth in claim 31 wherein said first element (416) is a first ring (417) with a first end (66) and a second end (64); said second enclosure (58) being disposed between said first (66) and said second ends (64), said second end (64) to open said second enclosure (58).

33. An assembly (410) as set forth in claim 32 wherein said second end (64) of said first ring (417) includes a projection (70) and a shoulder (72).

34. An assembly (410) as set forth in claim 31 wherein said first element (416) is a first ring (417) with a first end (66) and a second end (64); and wherein said first end (66) and said second end (64) of said first ring (417) are attached to said second enclosure (58) for rupturing said second enclosure (58).

\* \* \* \* \*